United States Patent
Gokaraju et al.

(10) Patent No.: US 6,900,356 B2
(45) Date of Patent: May 31, 2005

(54) POLYHYDROXY CURCUMINS HAVING ANTIOXIDANT ACTIVITY

(75) Inventors: Ganga Raju Gokaraju, Andhra Pradesh (IN); Venkata Subbaraju Gottumukkala, Andhra Pradesh (IN); Venkateswarlu Somepalli, Vijayawada (IN)

(73) Assignee: Laila Impex, Andhra Predesh (IN)

( * ) Notice: Subject to any disclaimer, the term of this patent is extended or adjusted under 35 U.S.C. 154(b) by 137 days.

(21) Appl. No.: 10/333,971

(22) PCT Filed: Apr. 18, 2001

(86) PCT No.: PCT/IN01/00090

§ 371 (c)(1),
(2), (4) Date: Jan. 24, 2003

(87) PCT Pub. No.: WO02/083614

PCT Pub. Date: Oct. 24, 2002

(65) Prior Publication Data

US 2003/0216600 A1 Nov. 20, 2003

(51) Int. Cl.$^7$ ............................ C07C 45/71; C07C 39/12
(52) U.S. Cl. ........................ 568/313; 568/333; 568/729
(58) Field of Search ................................ 568/313, 333, 568/729

(56) References Cited

U.S. PATENT DOCUMENTS 5,679,864 A   10/1997   Krackov et al. ............ 568/313

OTHER PUBLICATIONS

Artico, Marino, et al.; "Geometrically and Conformationally Restrained Cinnamoyl Compounds as Inhibitors of HIV–1 Integrase: Synthesis, Biological Evaluation, and Molecular Modeling;" *J. Medical Chem*, 41, pp. 3948–3960 (1998).
PCT International Preliminary Examination Report (5 pages total), which was completed on Apr. 23, 2003, for PCT Application No. PCT/IN01/00090.

*Primary Examiner*—Samuel Barts
*Assistant Examiner*—Sikarl A. Witherspoon
(74) *Attorney, Agent, or Firm*—Ladas & Parry

(57) ABSTRACT

This invention relates to novel polyhydroxy curcumins of the formula (I), wherein R and $R^1$ may be same or different and are selected from H, OH and $OCH_3$. This invention also includes a process for synthesising the above polyhydroxy curcumins by reacting substituted aromatic alhehydes with a diketone in the presence of boron oxide, alkyl borate and a primary or secondary amine catalyst. If desired, the resulting compounds can be deprotected by known means. These compounds are used as anti-oxidants.

19 Claims, No Drawings

POLYHYDROXY CURCUMINS HAVING ANTIOXIDANT ACTIVITY

TECHNICAL FIELD

Curcuma longa Linn or Turmeric is commonly used as a spice in many Asian and South Asian countries. Medicinal value of turmeric has been disclosed in Ayurveda, an ancient medical system practiced in India. Dried rhizomes of turmeric have been used as a preservative food colouring agent and for the treatment of skin disorders and for improving complexion.

Natural curcumins extracted and isolated from curcuma longa are reported to possess several pharmacological properties. Naturally occuring curcumins exhibit anti-oxidant, anti-mutagenic and anticarcinogenic properties. Isolation and separation of various curcumins from Curcuma longa rhizomes are found to be difficult and expensive. Successful attempts have been made to synthesise these naturally occuring products.

BACKGROUND OF THE INVENTION

Excellent bioprotective properties such as antioxidant, anticancer, anti-inflammatory, antifungal and free radical scavenging activity of curcumins have been receiving considerable attention from scientists and pharmacologist all over the world. Wound healing and antiviral properties of curcumins in addition to its ability for inhibition of superoxide generation by macrophoraging indicate the usefulness of these compounds against human immuno deficiency virus.

The above referenced bioprotective properties of curcumins are attributed to the presence of adjacent phenolic groups and the conjugated diketone moiety of the structure. Naturally occuring curcumin 3 represented by the following formula is found to exhibit better bioprotective activity than the corresponding methylated derivatives.

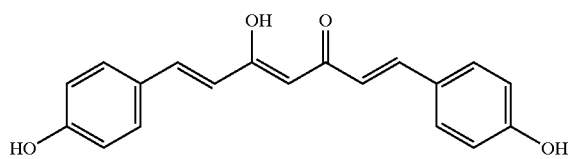

Curcumin 3

DISCLOSURE OF THE INVENTION

It has been found that novel synthetic polyhydroxycurcumins of the general formula I

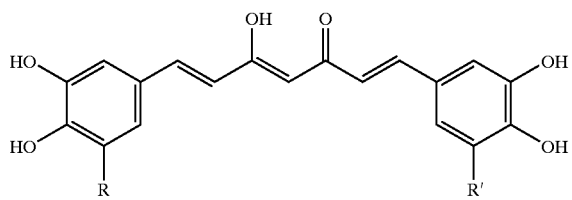

show better and improved bioprotective activities than the naturally occuring curcumins having lesser number of hydroxy groups. Exhanced activity of these polyhydroxy- curcumins may be based on the presence of catechol moieties in their structure.

This invention relates to polyhydroxy curcumins of the formula I

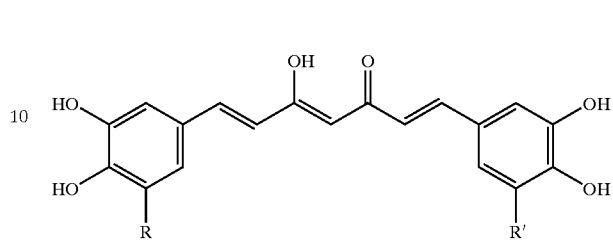

wherein R and $R^1$ may be same or different and are selected from H, OH and $OCH_3$.

Preferred compounds of the invention are (1) 1,7-bis(3,4-dihydroxy-5-methoxyphenyl)-3-hydroxy-1,3,6-heptatrien-5one; (2) 1,(7)-(3,4-dihydroxy-5-methoxyphenyl)-7(1)-(3,4-dihydroxyphenyl)-3-hydroxy-1,3,6-heptatriene-5-one; (3) 1(7)-3,4,5-trihydroxyphenyl)-7(1)-(3,4-dihydroxyphenyl)-3-hydroxy-1,3,6-heptatriene-5-one and (4) 1,7-bis(3,4,5-trihydroxyphenyl)-3-hydroxy 1,3,6-heptatriene-5-one.

This invention also includes a process for preparing the polyhydroxy curcumins of the formula I.

This process consists of reacting suitably substituted aromatic aldehydes with a diketone such as acetyl acetone in the presence of a polar, aprotic organic solvent water scavengers like $C_{1-5}$ alkylborates are added to the reaction mixture. The reaction is carried out by the addition of $B_2O_3$ to produce the boron complex as intermediate. The catalysts used are primary amines though it is found that 1,2,3,4 tetrahydroquinoline produces optimum yield of the tide compound. If protective groups are present in the substituted aldehydes treating with conventional agents like $AlCl_3$, pyridine and $CH_2Cl_2$ may demethylate the resulting reaction product. Polyhydroxy curcumins of the general formula I are separated from the reaction mixture in a known manner.

A preferred embodiment of the reaction scheme is given below:

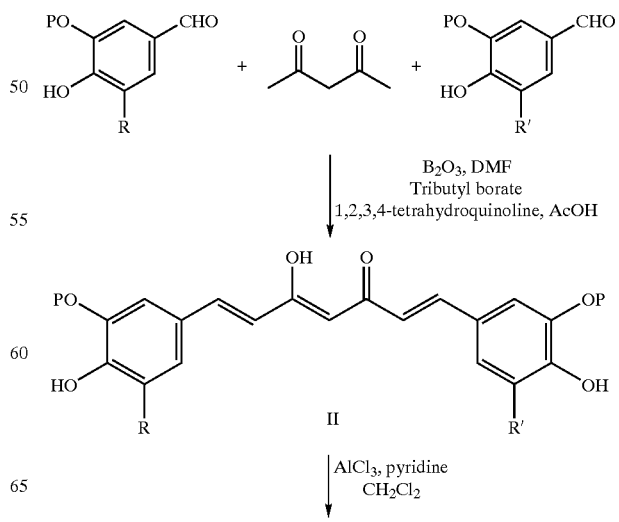

-continued

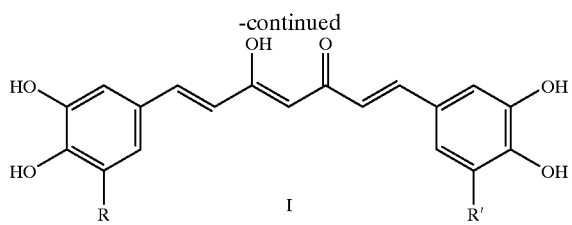

P is a protective group selected from $OCH_3$ and $OCH_2C_6H_5$. R and $R^1$ may be same or different and are H, OH and $OCH_3$. The hydroxy group at position 4 of the aromatic aldehyde may also be protected and subsequently deprotected.

The process for producing polyhydroxy curcumin of the formula I comprises the steps of reacting a substituted aromatic aldehyde preferably having protective substituents with a diketone in the presence of boron oxide, alkyl borate and a catalyst selected from a primary or secondary amine, in a polar, oprotic organic solvent and subsequently deprotecting the resulting product, if desired, to obtain polyhydroxy curcumins of the formula I.

Preferred embodiments of the process are described hereinafter by way of examples.

EXAMPLE I

To a solution of 400 mg of boric oxide in 1 ml of DMF solvent was added to 0.5 ml of acetyl acetone. 2.7 ml of tributylborate was then added and the reaction mixture was heated under stirring to 60–70° C. for about 15 min. 3,4-dibenzyloxy-5-methoxybenzyldehyde in 2 molar equivalents to acetyl acetone was then added and the mixture stirred. A mixture of 1,2,3,4 tetrahydroquinoline (0.1 ml) about 0.3 ml of glacial acetic acid and 1 ml of DMF was then added and the reaction mixture was heated to 100° C. for about 4 hours. The reaction mixture is then cooled and aqueous acetic acid was added to precipitate a solid. After an hour the precipitate was filtered and separated over silica gel column using chloroform-methanol mixture for elution. The compound obtained 1,7-bis(3,4-dibenzyloxy-5-methoxyphenyl)-3-hydroxy-1,3,6heptatrien-5-one.

This example is restricted to the deprotection step of the substituents of the compounds obtained in the above referenced example I. The product obtained therefrom is treated with 4:0 ml of N,N dimethylaniline, 25 ml of $CH_2Cl_2$ and 2.8 of aluminum chloride at 0–5° C. and the reaction mixture was slowly warmed to room temperature under stirring for about 16 hours. After acidifying with HCl, the reaction mixture was extracted with ethyl acetate and n-butanol. The combined organic layer was washed with brine and dried. The residue is purified over a column of silica gel using an eluent of chloroform and methanol mixture. The product obtained after concentration of the eluent is 1,7-bis(3,4,5-trihydroxy phenyl)-3-hydroxy-1,3,6-heptatriene-5-one.

Antioxidant and superoxide scavenging activity of the novel poly hydroxy curcumins was determined by Mc Cord and Fridovich method which depends on light induced superoxide generation by riboflavin and corresponding reduction of NBT. The assay mixture contains phosphate buffer, EDTA, NBT and riboflavin. Different concentration of the compounds were assessed and their optical densities measured before and after illumination. The percentage inhibition of superoxide production by the compounds of the invention was evaluated and compared with the absorbance value of control and experimental tubes.

The compounds of the invention are found to show better bioprotective activity like antioxidation and superoxide scavenging.

What is claimed is:

1. A polyhydroxycurcumin of general formula I:

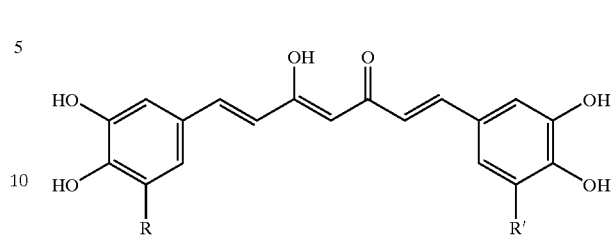

wherein R and $R^1$ are the same or different; wherein R and $R^1$ are each selected from the group consisting of H, OH, and $OCH_3$; wherein when R is OH, then $R^1$ is OH; wherein when R is $OCH_3$, then $R^1$ is $OCH_3$; and wherein when R is H, then $R^1$ is OH or $OCH_3$.

2. The polyhydroxycurcumin of the formula I as claimed in claim 1 which is 1,7-bis(3,4-dihydroxy-5-methoxyphenyl)-3-hydroxy-1,3,6-heptatriene-5-one.

3. The polyhydroxycurcumin of the general formula I as claimed in claim 1 which is 1(7)-3,4-dihydroxy-5-methoxyphenyl)-7(1)-(3,4,-dihydroxyphenyl)-3-hydroxy-1, 3,6-heptatriene-5-one.

4. The polyhydroxycurcumin of the general formula I as claimed in claim 1, which is 1(7)-3,4,5-trihydroxyphenyl)-7(1)-3-4-dihydroxyphenyl-3-hydroxy-1,3,6-heptatriene-5-one.

5. The polyhydroxycurcumin of the general formula I as claimed in claim 1, which is 1,7-bis(3,4,5-trihydroxyphenyl)-3-hydroxy-1,3,6-heptatriene-5-one.

6. The polyhydroxycurcumin of the general formula I as claimed in claim 1, wherein the polyhydroxycurcumin is selected from the group consisiting of: 1-[1,7-bis(3,4-dihydroxy-5-methoxyphenyl)-3-hydroxy 1,3,6-heptatriene 5-one; dihydroxycurcumin 2[1,7-bis (3,4-dihydroxy-5-methoxyphenyl)-7(1)- (3,4-dihydroxyphenyl)-3-hydroxy-1, 3,6-heptatriene-5-one; trihydroxycurcumin 3[1(7) 3,4,5-dihydroxy-5-methoxyphenyl)- 7(1)-(3,4-dihydroxyphenyl)-3-hydroxy-1,3,6-heptatriene-5-one; and tetrahydroxycurcumin-3[1,7-bis (3,4,5-trihydroxyphenyl)-3-hydroxy-1,3,6-heptatriene-5-one.

7. A process for producing a polyhydroxycurcumin of the general formula I as claimed in claim 1, wherein the process comprises the steps of reacting a substituted aromatic aldehyde with a diketone in the presence of boron oxide, alkyl borate and a catalyst selected from a primary amine and a secondary amine, in a polar, aprotic organic solvent to yield a resulting product and then optionally subsequently deprotecting the resulting product to obtain the polyhydroxycurcumin.

8. The process as claimed in claim 7, wherein said diketone is acetyl acetone, said alkyl borate is tributyl borate and said aromatic aldehyde is 3,4-dibenzyloxy-5-methoxybenzaldehyde.

9. The process as claimed in claim 7, wherein the catalyst used is 1,2,3,4-tetrahydroquinoline.

10. The process as claimed in claim 7, wherein said aromatic aldehyde is provided with methyl and benzyl protective groups.

11. The process as claimed in claim 7, wherein deprotection is by methods known per se.

12. The process as claimed in claim 10, wherein the reactants are deprotected by treating with chloride and pyridine.

13. A process for producing a polyhydroxycurcumin of the general formula I as claimed in claim 2, wherein the process comprises the steps of reacting a substituted aromatic aldehyde with a diketone in the presence of boron oxide, alkyl borate and a catalyst selected from a primary amine and a secondary amine, in a polar, aprotic organic solvent to yield a resulting product and then optionally subsequently deprotecting the resulting product to obtain the polyhydroxycurcumin.

14. A process for producing a polyhydroxycurcumin of the general formula I as claimed in claim 3, wherein the process comprises the steps of reacting a substituted aromatic aldehyde with a diketone in the presence of boron oxide, alkyl borate and a catalyst selected from a primary amine and a secondary amine, in a polar, aprotic organic solvent to yield a resulting product and then optionally subsequently deprotecting the resulting product to obtain the polyhydroxycurcumin.

15. A process for producing a polyhydroxycurcumin of the general formula I as claimed in claim 4, wherein the process comprises the steps of reacting a substituted aromatic aldehyde with a diketone in the presence of boron oxide, alkyl borate and a catalyst selected from a primary amine and a secondary amine, in a polar, aprotic organic solvent to yield a resulting product and then optionally subsequently deprotecting the resulting product to obtain the polyhydroxycurcumin.

16. A process for producing a polyhydroxycurcumin of the general formula I as claimed in claim 5, wherein the process comprises the steps of reacting a substituted aromatic aldehyde with a diketone in the presence of boron oxide, alkyl borate and a catalyst selected from a primary amine and a secondary amine, in a polar, aprotic organic solvent to yield a resulting product and then optionally subsequently deprotecting the resulting product to obtain the polyhydroxycurcumin.

17. A process for producing a polyhydroxycurcumin of the general formula I as claimed in claim 6, wherein the process comprises the steps of reacting a substituted aromatic aldehyde with a diketone in the presence of boron oxide, alkyl borate and a catalyst selected from a primary amine and a secondary amine, in a polar, aprotic organic solvent to yield a resulting product and then optionally subsequently deprotecting the resulting product to obtain the polyhydroxycurcumin.

18. The process as claimed in claim 7, wherein the substituted aromatic aldehyde has protective substituents.

19. The process as claimed in claim 8, wherein the catalyst used is 1,2,3,4-tetrahydroquinoline.

* * * * *